US008557960B2

(12) United States Patent
Kim et al.

(10) Patent No.: US 8,557,960 B2
(45) Date of Patent: Oct. 15, 2013

(54) PEPTIDE FOR AUGMENTING AND EXPRESSION OF BDNF AND PHARMACEUTICAL COMPOSITION FOR PREVENTION AND TREATMENT OF NEURODEGENERATIVE DISEASES INCLUDING ALZHEIMER'S DISEASE OR PARKINSON'S DISEASE, COMPRISING THE SAME

(75) Inventors: Kil Lyong Kim, Seoul (KR); Hong Gi Kim, Gyeonggi-do (KR); Woo Ram Jung, Gyeonggi-do (KR); Dong Ik Park, Incheon (KR); Min Kyoo Shin, Gyeongsangnam-do (KR)

(73) Assignee: Sungkyunkwan University, Gyeonggi-Do (KR)

( * ) Notice: Subject to any disclaimer, the term of this patent is extended or adjusted under 35 U.S.C. 154(b) by 0 days.

(21) Appl. No.: 12/934,029

(22) PCT Filed: Dec. 31, 2009

(86) PCT No.: PCT/KR2009/008018

§ 371 (c)(1),
(2), (4) Date: Jul. 6, 2011

(87) PCT Pub. No.: WO2011/055880

PCT Pub. Date: May 12, 2011

(65) Prior Publication Data

US 2012/0208747 A1  Aug. 16, 2012

(30) Foreign Application Priority Data

Nov. 6, 2009 (KR) .................. 10-2009-0106985

(51) Int. Cl.
*C07K 1/00* (2006.01)
*C07K 5/00* (2006.01)

(52) U.S. Cl.
USPC ................... 530/331; 530/300; 514/21.9

(58) Field of Classification Search
None
See application file for complete search history.

(56) References Cited

U.S. PATENT DOCUMENTS

| 5,512,661 A | 4/1996 | Shooter et al. |
| 5,696,080 A | 12/1997 | O'Brien et al. |
| 2007/0060526 A1 | 3/2007 | Longo et al. |
| 2008/0287650 A1* | 11/2008 | Tovi et al. ............ 530/317 |

FOREIGN PATENT DOCUMENTS

| WO | 0075176 | 12/2000 |
| WO | 03056925 | 7/2003 |
| WO | WO2009/136752 | * 5/2009 |

OTHER PUBLICATIONS

Wallace et al., Breakdown of different peptides by *Prevotella* (Bacteroides) *ruminicola* and mixed microorganisms from the sheep rumen. Current Microbiology vol. 26(1993), pp. 333-336.*
Eagle The Specific Amino Acid Requirements of a Mammalian Cell (Strain L) in Tissue Culture Journal of Biological Chemistry (1954) 839-852.*
International Search Report for International Patent Application No. PCT/KR2009/008018 dated Feb. 15, 2011.
Brown et al., "Studies on the Substrate Specificity of an *Escherichia coli* Peptidase", Biochem Biophys Res Commun. 1971, vol. 42(3): 390-397 (Table 1).
Wallace et al., "Breakdown of Different Peptides by *Prevotella* (Bacteroides) *ruminicola* and Mixed Microorganisms from the Sheep Rumen", 1993, Current Microbiology, vol. 26 pp. 333-336 (Table 1).
Davies, "The Role of Neurotrophins During Successive Stages of Sensory Neuron Development," Progress in Growth Factor Research, vol. 5, pp. 263-289, 1994.
Schnell et al, "Neurotrophin-3 Enhances Sprouting of Corticospinal Tract During Development and After Adult Spinal Cord Lesion," Letters to Nature, vol. 367, pp. 170-173, 1994.
Poo et al, "Phospholipase C-Y and Phosphoinositide 3-Kinase Mediate Cytoplasmic Signaling in Nerve Cone Guidance," Neuron, vol. 23, pp. 139-148, 1999.
Schinder et al, "The Neurotrophin Hypothesis for Synaptic Plasticity," TINS, vol. 23, pp. 639-645, 2000.
Lu, "BDNF and Activity-Dependent Synaptic Modulation," Cold Springs Harbor Laboratory Press, vol. 10, pp. 86-98, 2003.
Ikegaya et al, "Short Communication: BDNF Attenuates Hippocampal LTD via Activation of Phospholipase C: Implications for a Vertical Shift in the Frequency-Response Curve of Synaptic Plasticity," European Journal of Neuroscience, vol. 16, pp. 145-148, 2002.
Knipper et al, "Short Communication: Positive Feedback Between Acetylcholine and the Neurotrophins Nerve Growth Factor and Brain-Derived Neurotrophic Factor in the Rat Hippocampus," European Journal of Neuroscience, vol. 6, pp. 668-671, 1994.
Mesulam, Neuroplasticity Failure in Alzheimer's Disease: Bridging the Gap Between Plaque and Tangles, Neuron, vol. 24, pp. 521-529, 1999.
Phillips et al, "BDNF MRNA is Decreased in the Hippocampus of Individuals With Alzheimer's Disease," Neuron, vol. 7, pp. 695-702, 1991.
Holsinger et al, "Quantitation of BDNF MRNA in Human Parietal Cortex by Competitive Reverse Transcription-Polymerase Chain Reaction: Decreased Levels in Alzheimer's Disease," Molecular Brain Research, vol. 76, pp. 347-354, 2000.
Allen et al "Prfound and Selective Loss of Catalytic TRKB Immunoreactivity in Alzheimer's Disease," Biochemical and Biophysical Communications, col. 264, pp. 648-651, 1999.

(Continued)

*Primary Examiner* — Jeffrey Stucker
*Assistant Examiner* — Aurora M Fontainhas
(74) *Attorney, Agent, or Firm* — Casimir Jones, S.C.; Tanya A. Arenson

(57) ABSTRACT

Disclosed are peptides for augmenting the expression of BDNF (brain-derived neurotrophic factor) and a pharmaceutical composition for the prevention and treatment of Alzheimer's disease or Parkinson's disease, comprising the same. The peptides can induce the expression of BDNF in dopamine-reactive human cells, pass easily through the blood-brain barrier thanks to their low molecular weights and are almost free of cytotoxicity. Thus, they are useful in the prevention and treatment of neuropathies such as Alzheimer's disease or Parkinson's disease.

5 Claims, 3 Drawing Sheets

(56) References Cited

OTHER PUBLICATIONS

Figurov et al, "Regulation of Synaptic Responses to High-Frequency Stimulation and LTP by Neurotrophins in the Hippocampus," Letters to Nature, vol. 381, pp. 706-709, 1996.

Zuccato et al, "Loss of Huntingtin-Mediated BDNF Gene Transcirption in Huntington's Disease," Science, vol. 293, pp. 493-498, 2001.

Zuccato et al, "Brain-Derived Neurotrophic Factor in Neurodegenerative Diseases," Nature Review: Neurology, vol. 5, pp. 311-322, 2009.

Siegel et a, "Neurotrophic Factors in Alzheimer's and Parkinson's Disease Brain," Brain Research Reviews, vol. 33, pp. 199-227, 2000.

Seroogy et al, "Dopaminergic Neurons in Rat Ventral Midbrain Express Brain-Derived Neurotrophic Factor and Neurotrophin-3 MRNAs," The Journal of Comparative Neurology, vol. 342, pp. 321-334, 1994.

Porritt et al, "Inhibiting BDNF Expression by Antisense Oligonucleotide Infusion Causes Loss of Nigral Dopaminergic Neurons," Experimental Neurology, vol. 192, pp. 226-234, 2005.

Baquet et al, "Brain-Derived Neurotrophic Factor is Required for the Establishment of the Proper Number of Dopaminergic Neurons in the Substantia Nigra Pars Compacta," The Journal of Neuroscience, vol. 25, pp. 6251-6259, 2005.

Mogi et al, "Brain-Derived Growth Factor and Nerve Growth Factor Concentrations are Decreased in the Substantia Nigra in Parkinsons's Disease," Neuroscience Letters, vol. 270, pp. 45-48, 1999.

Dunman et al "A Neurotrophic Model for Stress-Related Mood Disorders," Biol Psychiatry, vol. 59, pp. 1116-1127, 2006.

Smith et al, "Effects of Stress in Neurotrophic Factor Expression in the Rat Brain," Annals of the New York Academy of Sciences, vol. 771, pp. 234-239, 1995.

Sheline et al "Untreated Depression and Hippocampal Volume Loss," Am J. Psychiatry, vol. 160, pp. 1516-1518, 2003.

Tsuzaka et al, "Role of Brain-Derived Neurotrophic Factor in Wobbler Mouse Motor Neuron Disease," Department of Neurology and Neurosciences, pp. 474-480, 2001.

Nitta et al, "Diabetic Neuropathies in Brain are Induced by Deficiency of BDNF," Neurotoxicology and Teratology, vol. 24, pp. 695-701, 2002.

Han et al, "BDNF Protects the Neonatal Brain From Hypoxic-Ischemic Injury in Vivo via the ERK Pathway," The Journal of Neuroscience, vol. 20, pp. 5775-5781, 2000.

Schabitz et al, "Intravenous Brain-Derived Neurotrophic Factor Enhances Poststroke Sensorimotor Recovery and Stimulates Neurogenesis," Stroke, Journal of the American Heart Association, vol. 38, pp. 3165-2172, 2007.

* cited by examiner

* $p < 0.0001$ versus MPP+

* $p < 0.001$,  $p < 0.01$, * $p < 0.05$ versus Aβ

PEPTIDE FOR AUGMENTING AND EXPRESSION OF BDNF AND PHARMACEUTICAL COMPOSITION FOR PREVENTION AND TREATMENT OF NEURODEGENERATIVE DISEASES INCLUDING ALZHEIMER'S DISEASE OR PARKINSON'S DISEASE, COMPRISING THE SAME

FIELD OF THE INVENTION

The present invention relates to a novel peptide for inducing the expression of BDNF which plays an important role in various functions including the growth and differentiation of neurons, learning and memory, and anti-depression activity, and a pharmaceutical composition for the prevention and treatment of Alzheimer's disease or Parkinson's disease, comprising the same as an active ingredient.

BACKGROUND OF THE INVENTION

Neurotrophic factors regulate the survival and differentiation of neurons during development (Davies, 1994) and are known to be involved in a diversity of different functions including the maintenance of neuronal structures, the activity of ion channels, the release of neurotransmitters, and axon path-finding during an organism's life span (Schnell et al., 1994; Song and Poo, 1999; Schinder and Poo, 2000). There are several neurotrophic factors such as, nerve growth factor (NGF), brain-derived neurotrophic factor (BDNF), neurotrophin-3 (NT-3), and neurotrophin-4/5 (NT-4/5)

BDNF, acting on neurons of the central nervous system (CNS), is expressed predominantly in the hippocampus, the cortex, and the synapses of the basal forebrain, which are areas vital to learning, memory, and higher thinking. The BNDF expressed in these areas serves as an important regulator of synaptic transmission and synaptic plasticity (which forms a neurobiochemical basis for learning and memory formation and a recognition process) (Lu B, 2003). Particularly, BDNF promotes long-term potentiation (LTP), which is one of the cellular mechanisms which underlies learning and memory, while reducing long-term depression (LTD) (Ikegaya, Y. et al., 2002; Huber, K. et al., 1998). The roles of BDNF arise in part because BDNF and its receptor TrkB (tropomyosin-related kinase B) are localized to glutamate synapses.

As explained above, BDNF plays a regulatory role in synaptic transmission and synaptic plasticity, and these roles are significantly important with respect to various diseases, as well as inter alia, cerebral degenerative diseases, especially, Alzheimer's disease (AD), Parkinson's disease (PD), stress-induced depression, stroke, Huntington's disease, cerebral ischemia, neurodegenerative diseases and diabetic neuropathy. BDNF is highly correlated with these diseases.

Cholinergic neurons of the forebrain degenerate in Alzheimer's disease ("AD"), leading to acetylcholine reduction and subsequent cognitive deterioration (Murer M G et al., 2001). With respect to AD, BDNF has been shown to promote the survival and differentiation of basal forebrain cholinergic neurons. Interestingly, in these neurons, BDNF is also known to stimulate the release of acetylcholine (Knipper M et al., 1994). These preclinical observations suggest that deficits of BDNF synthesis might participate in the deterioration of the cellular homeostasis that leads to AD. In addition, it has been proposed that AD is due to the failure of neuroplasticity, which causes the loss of synaptic contacts and may lead to neuropathological and clinical manifestations (Mesulam M M., 1999). Postmortem clinical evidence of AD patients has shown that the expression of BDNF and its receptor trk B is significantly decreased in the hippocampus and the cortex, which are cerebral areas responsible for learning and memory (Phillips H S et al., 1991; Holsinger R M et al., 2000; Allen S J et al., 1999). BDNF is known to regulate LTP (long-term potentiation), which is in these areas a cellular mechanism of learning and memory through synaptic plasticity (Figurov, A. et al., 1996). Therefore, the decrease in BDNF expression is thought to induce the functional reduction of recognition and memory-related processes, causing Alzheimer's disease (C Zuccato and Elena Cattaneo, 2009).

Parkinson's disease is a debilitating movement disorder resulting from a massive loss of substantia nigral dopaminergic neurons and a depletion of striatal dopamine. Cognitive impairment is another feature of patients who have Parkinson's disease. Among the theories suggested to explain the etiology of Parkinson's disease, neurotrophic factors are expected to play an important role in protecting dopaminergic neurons (Siegel G J and Chauhan N B., 2000). Inter alia, BDNF is well known to interact with dopaminergic neurons. Dopaminergic neurons are in all of the ventral midbrain, the substantia nigra and the ventral tegmental area (Seroogy K B et al., 1994). Reduced expression of BDNF within the substantia nigra is accompanied by a significant deterioration in the dopaminergic neurons (Porritt M J et al., 2005). Also, BDNF is required for the establishment of the proper number of dopaminergic neurons in the substantia nigra pars compacta (Baguet Z C et al., 2005).

Postmortem studies of PD patients has revealed that the expression level of BDNF was remarkably reduced in the striatal dopaminergic neurons of such patients, indicating that there is a correlation between the reduced number of dopaminergic neurons and a shortfall in BDNF biosynthesis in Parkinson's disease (Mogi M et al., 1999; Howells D W et al., 2000).

In society these days, there is a rapid increase in the population of people who are suffering from stress-related mood disorders such as major depression. Stress is now known to cause nervous prostration and to reduce the volume of various brain regions including the hippocampus (Duman, R. S, and Monteggia, L. M. 2006) as well as the mRNA expression level of hippocampal BDNF (Duman, R. S, and Monteggia, L. M. 2006 Smith, M. A. et al., 1995). In practice, postmortem evidence has shown that the expression level of BDNF in the brain of depressed patients was significantly lower than in the brain of healthy persons. In addition, imaging studies have revealed a shrinkage of the hippocampus in the brain patients with major depression (Sheline, Y. I et al., 2003). It has been suggested that a variety of antidepressants can be used to treat stress-related mood disorders. These antidepressants are commonly intended to increase BDNF mRNA levels in the hippocampus or prefrontal cortex or in both regions (Duman, R. S, and Monteggia, L. M. 2006). On the basis of these results, the so-called 'neurotrophin hypothesis of depression' has been proposed. This hypothesis states that antidepressant treatments achieve their therapeutic effects by increasing the expression of BDNF in the hippocampus or the prefrontal cortex (Duman, R. S, and Monteggia, L. M. 2006).

As described hereinbefore, BDNF is involved in the maintenance of neural structures, the activity of ion channels and the release of neurotransmitters as well as playing an important role in the growth and differentiation of neurons, learning and memory, and anti-depression activity. Together with these various functions, BDNF is highly correlated with the onset of various diseases including Alzheimer's disease, Parkinson's disease, chronic stress-related mood disorder such as major depression, stroke (Schabitz et al., Stroke, 38:2165-

2172, 2007), Huntington's disease (Zuccato C et al., Science 293, 20, July 2001), cerebral ischemia (Han B H et al., the Journal of neuroscience, 2000, 20(15):5775-5781, Aug. 1, 2000), neurodegenerative disease (Tsuzaka K et al., Muscle Nerve. 24(4):474-80, April 2001) and diabetic neuropathy (Nitta A et al., Neurotoxicology and Teratology, 24:695-701, 2002).

Accordingly, a variety of methods have been suggested for applying BDNF to the treatment of these diseases. PCT Publication No. WO2003/056925 describes the treatment of neurodegenerative diseases by delivering BDNF to the entorhinal cortex with a micropump. U.S. Pat. No. 5,512,661 discloses a chimeric protein which has neurotrophic activity and which consists essentially of BDNF and partially of NGF. However, BDNF itself, which is a macromolecule with a molecular weight of 14 kDa, cannot pass through the blood-brain barrier (BBB). The likelihood of enzymatic degradation degrades the reliability of BDNF because it cannot be delivered safely to the targets. Further, a limitation is imparted to the oral dosage of the neutrophic factor. As solutions to these problems, non-peptide mimetics of BDNF were suggested in PCT WO 2000/075176 and U.S. Patent Publication No. 2007-060526. Thanks to their low molecular weights, these mimetics can advantageously pass through the blood brain barrier and can overcome the problem of short life span; however, they are cytotoxic and cause side effects

SUMMARY OF THE INVENTION

Technical Problem

Leading to the present invention, intensive and thorough research, conducted by the present inventors, aiming to overcome the problems encountered in the prior art, resulted in finding substances which are capable of induce the expression of BDNF in hippocampal neurons, hippocampus and cerebral cortex tissues and passing easily through the blood-brain barrier without cytotoxicity.

Technical Solution

It is an object of the present invention to provide a peptide for augmenting the expression of BDNF in dopamine-reactive, human cell lines.

It is another object of the present invention to provide a pharmaceutical composition for the prevention and treatment of neuropathies caused by a lack of BDNF, such as Alzheimer's disease and Parkinson's disease, comprising a therapeutically effective amount of the peptide.

It is a further object of the present invention to provide a method for treating neuropathies, comprising administering the peptide or the pharmaceutical composition in a therapeutically effective amount.

Advantageous Effect

The peptides of the present invention, consisting of two or three amino acid residues, can augment the expression of BDNF. They show no cytotoxicity and can easily pass through the blood-brain barrier thanks to the low molecular weights thereof. Therefore, the peptides of the present invention are useful for preventing and treating neuropathies such as Alzheimer's disease or Parkinson's disease.

DESCRIPTION OF THE PREFERRED EMBODIMENTS

Best Mode

In accordance with an aspect thereof, the present invention provides a peptide for augmenting the expression of BDNF, comprising an amino acid sequence represented by the following formula:

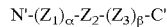

wherein N' stands for the N-terminus of the peptide, C' stands for the C-terminus of the peptide; $Z_1$ is E, G, H, L, M, P, R or T; $Z_2$ is A, D, M, T or V◯|⊐ ; $Z_3$ is A, D, E, F, G, H, I, K, Q, R, S or Y; α is 0 or 1; and β is 0 or 1.

In a preferred embodiment, the present invention provides a peptide having the amino acid sequence represented by the following formula:

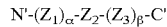

Wherein
$Z_1$ is G, M, or R,
$Z_2$ is D, T, or V, or
$Z_3$ is E, F, G, or Q.

In the peptide represented by N'-$(Z_1)_\alpha$-$Z_2$-$(Z_3)_\beta$-C' according to another preferred embodiment of the present invention, $Z_1$ is G, M, or R, $Z_2$ is D, T or V, and $Z_3$ is F, G or Q. In a further embodiment, the peptide of the present invention has an amino acid sequence selected from the group consisting of M-V-G, M-V-Q, G-V-G, R-V-G, M-D-G, M-T-G, M-V-F, M-V and V-G. The dipeptide M-V or V-G may pass through the blood-brain barrier more easily.

Using the peptide library technique, so-called PS-SPCL (Positional Scanning-Synthetic Peptide Combinatorial Library), amino acid residues which allow the most effective induction of BDNF at each position are chosen. These amino acid residues are combined with each other to afford di- or tri-peptides. The effect of the peptides on BDNF expression can be determined at a cellular level by RT-PCR and Western blotting.

In an embodiment, the murine hippocampal cell line HT22 was seeded at a density of $5 \times 10^4$ cells/well on 24-well plates and cultured for 12 hrs and for an additional 12 hours in the presence of a prepared PS-SPCL stock. Thereafter, proteins were obtained using a RIPA (Radio-immunoprecipitation Assay) buffer under the protection of a protease inhibitor and quantitatively analyzed for BDNF using ELISA (Enzyme-Linked ImmunoSorbent Assay).

Figure 1:
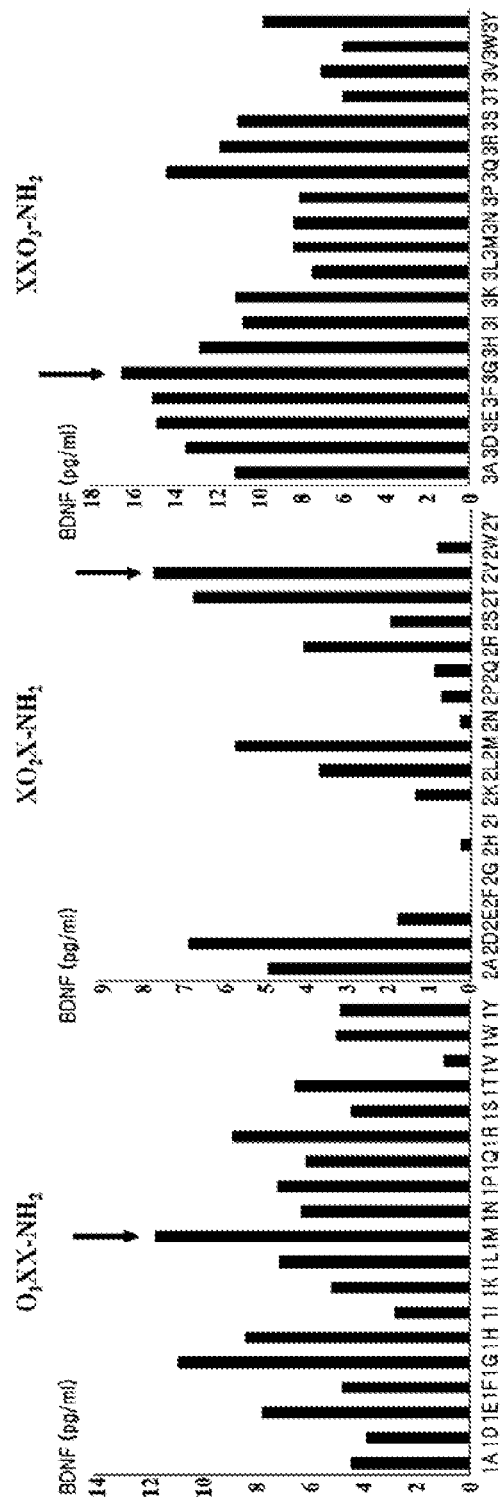
FIG. 1 is of graphs showing the expression levels of BDNF by amino acid residues at each position of tripeptides as measured by PS-SPCL (Positional Scanning-Synthetic Peptide Combinatorial Library).

BDNF was observed, as shown in FIG. 1, to be highly induced by the peptides which employed E (Glutamic acid), G (Glycine), H (Histidine), L (Leucine), M (Methionine), P (Proline), R (Arginine) or T (Threonine) at the first position, A (Alanine), D (Aspartic acid), M (Methionine), T (Threonine) or V (Valine) at the second position, and A (Alanine), D (Aspartic acid), E (Glutamic acid), F (Phenylalanine), G (Glycine), H (Histidine), I (Isoleucine), K (Lysine), Q (Glutamine), R (Arginine), S (Serine) or Y (Tyrosine) at the third position. Preferably, the peptides which employ M, G or R at the first position, V, D or T at the second position, or Q, G or F at the third position can effectively induce the expression of BDNF.

In another embodiment, the peptides of the present invention are acetylated or amidated at the N- or C-terminus thereof, respectively. This modification at both termini not only converts the charged molecules into neutral ones which is a feature that is advantageous with regards to cell penetration, but also increases the stability of the peptides by preventing enzymatic degradation. Alternatively, the peptides may be modified with an N-terminal blocking group) and/or a C-terminal blocking group which functions to prevent degradation or reaction during delivery to the target cells. In a preferred embodiment, the peptide may have an amino sequence of Ac-M-V-G or M-V-G-$NH_2$.

In accordance with another aspect thereof, the present invention provides a pharmaceutical composition for the prevention and treatment of neuropathies, comprising the peptide in a therapeutically effective amount.

Examples of the neuropathies include Alzheimer's disease, Parkinson's disease, chronic stress-related mood disorder, stroke, Huntington's disease, schizophrenia, obsessive compulsive disorder, Rett syndrome, dementia, anorexia nervosa, bulimia nervosa, obesity, cerebral ischemia, neurodegenerative disease, and diabetic neuropathy, but are not limited thereto. Generally, the pharmaceutical composition may comprise a pharmaceutically acceptable, non-toxic vehicle as well as the active ingredient and may be formulated together with the vehicle into forms of varying dosages. The pharmaceutical composition may be administered as a preventive or curing agent for neuropathies.

The pharmaceutically acceptable vehicles suitable for use in various dosage forms comprise all types of diluents or solvents, fillers, spraying agents, binders, dispersants, disintegrants, surfactants, lubricants, excipients, and wetting agents. In addition, if necessary, general dissolution auxiliaries, buffers, preservatives, colorants, flavors and sweeteners may be used in combination.

No limitations are imparted to the dosage form of the pharmaceutical composition according to the present invention, and it may be set to correspond to the therapeutic purpose. For example, the pharmaceutical composition may be formulated into oral dosage forms such as tablets, capsules, granules, pills, syrups, liquids, emulsions, suspensions, etc. or non-oral dosage forms such as injections (subcutaneous, intravenous, intramuscular, intraperitoneal, etc.), suppositories, etc. Preferable is an oral dosage preparation.

In addition, intracellular delivery techniques well known in the art may be employed to carry the peptide into cells. Among them are the use of microinjection, electroporation, cations, liposomes, and PTD (protein transduction domain).

Various dosage forms may be prepared using typical methods. For example, for preparation of oral dosage forms such as tablets, capsules, granules and pills, an excipient such as white sugar, lactose, glucose, starch and mannitol; a binder such as syrup, Arabic rubber, sorbitol, tragacanth rubber, methylcellulose and polyvinylpyrrolidone; a disintegrant such as starch, carboxymethyl cellulose and calcium salt thereof, microcrystalline cellulose and polyethyleneglycol; a lubricant such as talc, magnesium stearate, calcium stearate and silica; and a wetting agent such as sodium laurate and glycerol may be formulated in combination with the active ingredient in a typical manner.

For preparation of injections, liquids, emulsions, suspensions and syrups, a solvent for dissolving the active ingredient, such as ethyl alcohol, isopropyl alcohol, propylene glycol, 1,3-butylene glycol, polyethylene glycol and caster oil; a surfactant such as sorbitol fatty acid ester, polyoxyethylene sorbitol fatty acid ester, polyoxyethylene ester, hydrogenated caster oil and lecithin; a cellulose derivative such as sodium carboxymethyl cellulose and methyl cellulose; a suspending agent for natural rubber such as tragacanth and Arabic rubber; and, a preservative such as paraoxybenzoic acid ester, benzalconium chloride and sorbitan fatty acid salt, may be used in combination with the active ingredient.

For suppositories, the composition of the present invention may be formulated with a conventional base such as polyethylene glycol, lanoline, and cocoa butter.

The specific therapeutically effective dose level for any particular patient may vary depending on a variety of factors, including the route of administration, the dosage form, the patient's age, weight and sensitivity, the severity of the disease, etc. In an embodiment, the peptide contained in the pharmaceutical composition may be administered at a dose of from 0.1 μg/kg/day to 10 μg/kg/day.

The pharmaceutical composition of the present invention may be administered to mammals such as rats, mice, poultry and humans via various routes. Any administration route is possible. For instance, the pharmaceutical composition may administered orally or injected subcutaneously, intravenously, intramuscularly, intranasally, intraperitoneally, intrarectally, intrauterinely, or intracerebroventricularly. Having almost no toxicity and no side effects, the peptides of the present invention can be safely administered over the long-term.

In accordance with a further aspect thereof, the present invention provides a method for treating neuropathies, comprising administering the peptide or the pharmaceutical composition in a therapeutically effective amount to a subject in need thereof.

The term "subject", as used herein, is intended to refer to a patient suffering from a neuropathy which is induced directly or indirectly by the BDNF level, and the condition of which takes a favorable turn when the peptide or the pharmaceutical composition is administered thereto. Subjects include mammals such as humans, horses, sheep, pigs, goats, dogs, cats, etc. Mammals bred in zoological gardens and pets or sport mammals also fall within the scope of the subject. Preferable are humans.

As used herein, the term "administration" is intended to mean the introduction of the pharmaceutical composition of the present invention to a subject using any appropriate method. As long as it ensures the arrival of the composition of the present invention to a tissue of interest, any route may be used for the administration. For example, the composition of the present invention may be administered orally or parenterally. In addition, the administration may be performed with the aid of an instrument adapted for delivering the pharmaceutical composition to target cells. The peptides or the pharmaceutical composition of the present invention may be administered alone or in combination with other therapeutics. In this case, they are administered sequentially or simultaneously together with conventional therapeutics.

As used herein, the term "treatment" means an approach to obtaining a beneficial or intended clinical result. In the context of the present invention, the beneficial or intended clinical result includes the alleviation of symptoms, a reduction in the severity of the disease, steadying diseases in a non-advanced state, delaying the progress of a disease, and improvement or alleviation of disease conditions.

Examples of the neuropathies include Alzheimer's disease, Parkinson's disease, chronic stress-related mood disorder, stroke, Huntington's disease, schizophrenia, obsessive compulsive disorder, Rett syndrome, dementia, anorexia nervosa, bulimia nervosa, obesity, cerebral ischemia, neurodegenerative disease, and diabetic neuropathy, but are not limited thereto.

In accordance with a further aspect thereof, the present invention provides a polynucleotide consisting of a DNA sequence coding for the peptide. The polynucleotide includes equivalent nucleotide sequences, that is, codon-degeneracy sequences which are different in sequence, but encode the same peptides. The pharmaceutical composition of the present invention may comprise a polynucleotide consisting of a DNA sequence coding for the peptide or an equivalent nucleotide sequence, that is, a vector comprising codon-degeneracy sequences which are different in DNA sequence from each other, but encode the same peptide. A gene delivery method of the nucleotide sequences is also included within the scope of the present invention. The gene delivery of the nucleotide sequences may be performed using a well-known method. For example, gene carriers, including viral vectors such as retroviral vectors, adenoviral vectors, and adeno-associated viral vectors, and non-viral vectors such as cationic polymers, e.g., liposomes, plylysine, polyethylenimine (PEI), protamine, histone, polyester amines, and derivatives thereof, micelles, emulsions, nanoparticles, etc. may be employed. In addition to vector systems, peptides may be used to effectively deliver the nucleotide sequences to cells.

In accordance with an aspect thereof, the present invention provides a method for augmenting the expression of BDNF in hippocampal tissues and cerebral cortex tissues, using one of the peptides. In a preferred embodiment, the present invention provides a method for augmenting the expression of BDNF in dopamine-reactive, human cells. The peptide may be injected as it is or in the form of a polynucleotide or a vector containing it into a subject.

MODES FOR INVENTION

A better understanding of the present invention may be obtained through the following examples which are set forth to illustrate, but are not to be construed as limiting the present invention.

Example 1

Peptide Selection through PS-SPCL

In order to excavate peptides for augmenting BDNF expression, a PS-SPCL trimer package stock, afforded from the peptide library of Postech Biotech Center, was used. The PS-SPCL (Positional Scanning-Synthetic Peptide Combinatorial Library) employed in the present invention is a pool of tripeptides in which any amino acid residue except cysteine may take the first position while amino acid residues at the second and the third position are fixed. In this manner, effective amino acid residues at each position may be determined. Using the library therefore, amino acid sequences which are the most effective in stimulating the expression of BDNF could be obtained.

First, the murine hippocampal neuronal cell line HT22 was seeded at a density of $5 \times 10^4$ cells/well, a total of 57 wells into 24-well plates (SPL) and incubated at 37° C. for 12 hrs in a 5% $CO_2$ incubator (VISION). After spinning down a PS-SPCL trimer package stock, 15 µL of cell culture D.W. (distilled water) was added to the tubes which were then tapped and spun down. The prepared PS-SPCL trimer package stock was added in an amount of 15 µL per well to the 24-well plates in which HT22 cells had been grown, followed by incubation for 12 hrs. Afterwards, the medium was aspirated off from each well and the cells were washed twice with 1 mL of 1×PBS (Potassium persulfate). A protease inhibitor (Amersham) was prepared at a concentration of 10 µL/mL of RIPA and added to each well. Using a cell lifter (Corning), the cell lysates were collected into 1.5 mL tubes. After centrifugation at 4° C. and 9000 rpm for 5 min (MICRO 17TR, Hanil Science Industrial Co., Ltd) to pelletize the cell membranes, the supernatants which contained proteins were transferred into new 1.5 mL tubes and quantitatively measured for protein content using a Bradford assay.

BDNF expression levels were determined using ELISA (Enzyme-linked immunosorbent assay (BDNF ELISA Kit, Promega) according to the manufacturer's protocol. The amino acid residues at each position in the tri-peptides which induced the high expression levels of BDNF are given in FIG. 1.

Example 2

Assay for BDNF Expression in Dopamine-Reactive Human Cell Line SH-SY5Y

In order to measure the effect of increasing BDNF expression, synthetic di- or tri-peptides NP 2 to 9 were prepared, as shown in Table 1, below, by combining at each position the amino acids which were found to be effective for inducing BDNF expression, on the basis of the results of Example 1.

TABLE 1

| Peptides | Amino Acid Sequence |
| --- | --- |
| Neuropep-2 (NP2) | Met-Val-Gln (MVQ) |
| Neuropep-3 (NP3) | Gly-Val-Gly (GVG) |
| Neuropep-4 (NP4) | Arg-Val-Gly (RVG) |
| Neuropep-5 (NP5) | Met-Asp-Gly (MDG) |
| Neuropep-6 (NP6) | Met-Thr-Gly (MTG) |
| Neuropep-7 (NP7) | Met-Val-Phe (MVF) |
| Neuropep-8 (NP8) | Met-Val (MV) |
| Neuropep-9 (NP9) | Val-Gly (VG) |

SH-SY5Y cells were seeded at a density of $2 \times 10^5$ cells/well into 6-well plates (NUNC) and incubated at 34° C. for 12 hrs in a 5% CO2 incubator and then for an additional 12 hrs in the presence of one of NP 2 to 9 at a concentration of 1 pM, 10 pM, 100 pM, 1 nM, 10 nM, 100 nM, or 1 µM. The cells in each well were washed twice with 1 mL of 1×PBS (potassium persulfate), treated with 10 µL of protease inhibitor (Amersham) per 1 mL of RIPA, and collected into 1.5 mL tubes using a cell lifter (Corning). After centrifugation at 4° C. and 9000 rpm for 5 min (MiCRO 17 TR, Hnil Science Industrial Co., Ltd.) to pelletize cell membranes, the supernatants containing proteins were transferred into new 1.5 mL tubes and quantitatively measured for protein level using a Bradford assay.

Figure 2:
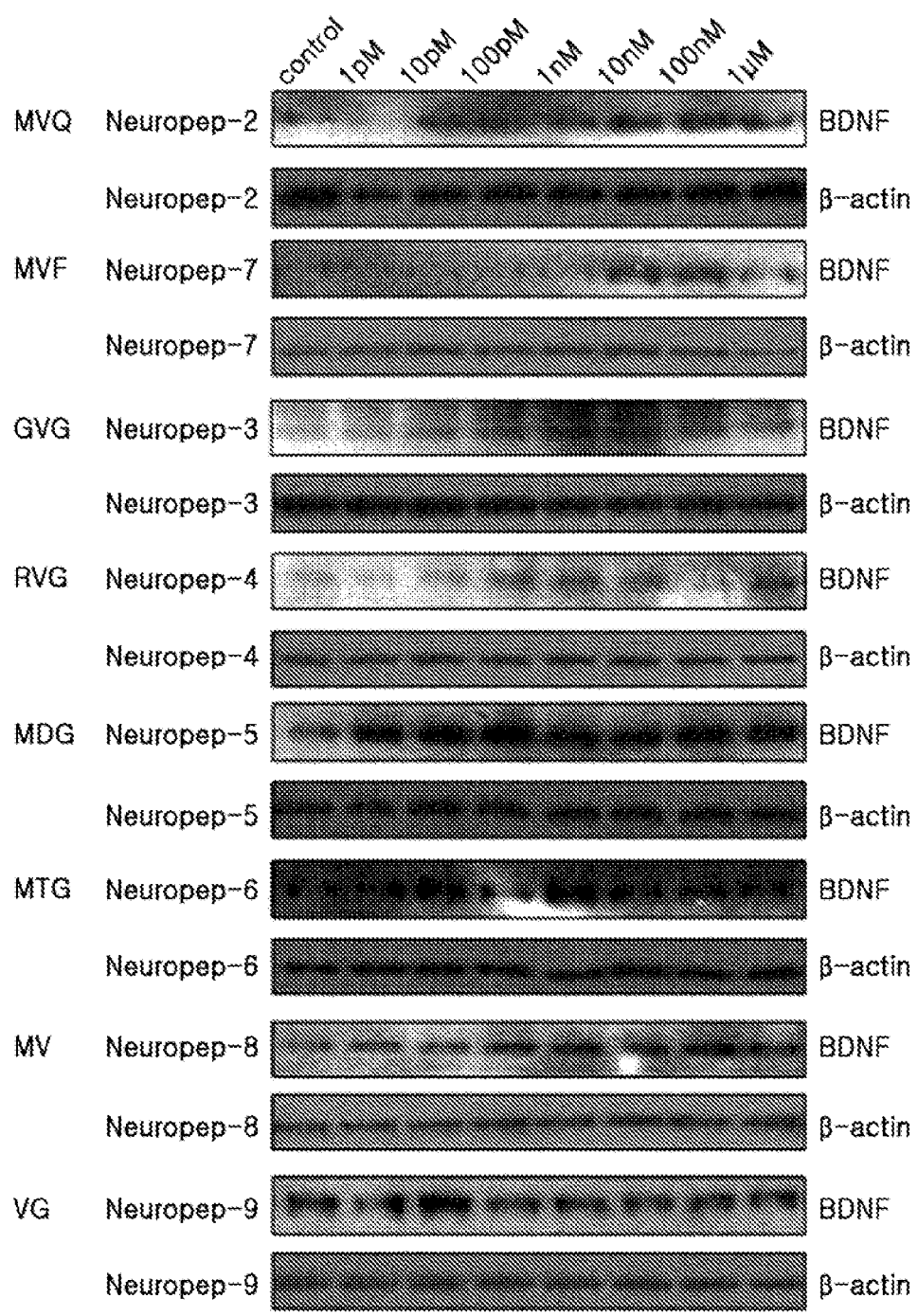
FIG. 2 is of photographs showing the expression levels of BDNF in SH-SY5Y cells treated with the synthetic peptides NP2 to NP9.

20 µL of each sample was loaded onto 15% acrylamide gel, prepared using a 1.5 mm Western blotting gel caster (Bio-Rad), and run for 2.5 hrs in the presence of an electric field of 100 V using an electrophoresis power supply (EPS 601, Amersham). The proteins run on the gel were transferred onto a PVDF membrane (Polyvinylidene Difluoride, Millipore) at 400 mA for 2.5 hrs in a transfer tank (Mighty small transphor, Amersham) using an electrophoresis power supply (EPS301, GE healthcare). The PVDF membrane was blocked for 1 hr with 7% skim milk (Difco™ Skim milk, BD) and incubated overnight with a mouse anti-human BDNF monoclonal antibody at a dilution ratio of 1:500. Thereafter, the membrane was washed for 2 hrs 0.05% TBST (Tris-Buffered Saline Tween 20) (this buffer was replaced every hour) and incubated for 1 hr with goat anti-mouse IgG:HRP (IgG:Horseradish Peroxidase Conjugate, SC-2005, Santa Cruz Biotechnology) at a ratio of 1:500. After washing the membrane with 0.05% TBST for 2 hrs (the buffer was replaced every hour), proteins were detected using a chemiluminescent HRP substrate kit (Millipore), and the results are shown in FIG. 2. As seen in FIG. 2, higher relative levels of BDNF to β-actin were observed in the experimental groups than in the control.

Analytically, all peptides showed activity and induced BDNF expression, but slightly differed from one to another in terms of effective concentration. In more detail, the concentration at which an expression effect was exerted by the peptides fell within a range of from 10 nM to 100 nM for NP-2 and NP-7, from 1 nM to 10 nM for NP-3, from 100 pM to 1 nM for NP-4, from 10 pM to 100 pM for NP-5 and NP-9, from 10 pM to 1 nM for NP-6, and from 1 nM to 100 nM for NP-8. Further, even a very small amount of NP-5 and NP-6 could augment BDNF expression. As for NP-9, which consists of two amino acid residues, it was used at the same or less than was the amount of the tripeptides so as to induce BDNF expression.

Example 3

Anti-Parkinson's Disease Effect

SH-SY5Y cells were seeded at a density of 5×10³ cells/well on 96-well plates (FALCON), incubated at 34° C. for 12 hrs in a 5% CO2 incubator, and treated for 12 hrs with 100 nM of NP-2, 10 nM of NP-7, 10 nM of NP-3, 100 pM of NP-4, 100 pM of NP-5, 10 pM of NP-6, 1 nM of NP-8, or 10 pM of NP-9. Thereafter, the media containing various concentrations of LDH and 10% FBS were substituted with an assay medium containing 1% FBS before incubation for 24 hrs with 2.5 mM MPP+ (D048, Sigma). The assay medium was free of phenol-red so that the medium could be monitored for color change while the reaction between released LDH and the reagents was ongoing. Then, the LDH reactant, composed of the enzyme and the dye, was incubated at RT for 10 min with the assay medium and the reaction was terminated with the stop solution of the assay kit, followed by measuring absorbance at 492 nm and 690 nm on an ELISA reader. This LDH assay was performed in triplicate on three separate media.

Figure 3:
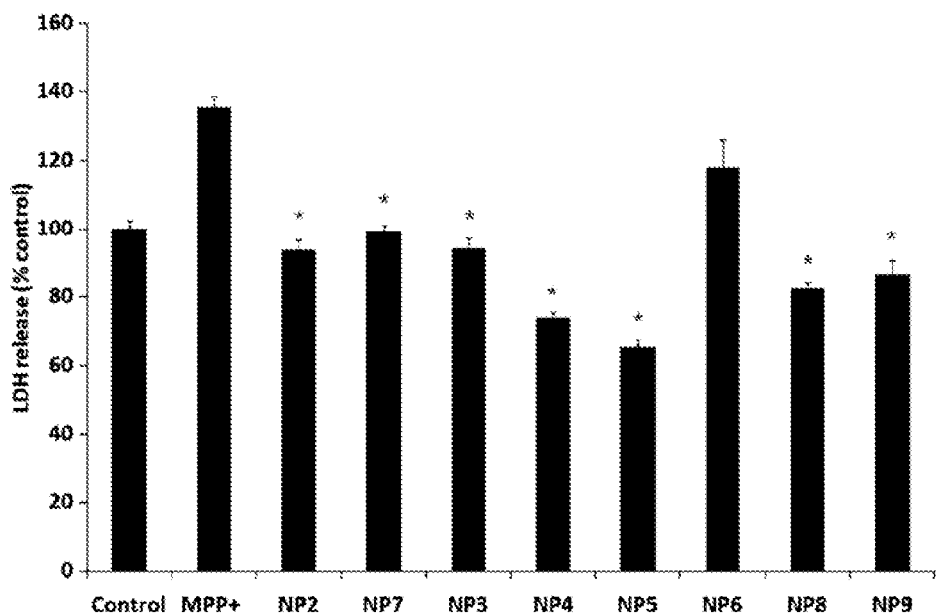
FIG. 3 is a graph showing the cytoprotective effects of the synthetic peptides NP2 to NP9 upon LDH (lactate dehydrogenase) assay thereof for anti-Parkinson's disease activity.

The assay results are shown in FIG. 3 in which values of experimental groups are represented as percentages relative to the control set as 100%. As is apparent from the data of FIG. 3, all the experimental groups exhibited lower LDH releases than did the MPP+-treated group, indicating that the peptides of the present invention are cytoprotective against and therapeutic for Parkinson's disease.

Example 4

Anti-Alzheimer's Disease Effect

SH-SY5Y cells were seeded at a density of 5×10³ cells/well on 96-well plates (FALCON), incubated at 34° C. for 12 hrs in a 5% CO2 incubator, and treated for 12 hrs with 100 nM of NP-2, 10 nM of NP-7, 10 nM of NP-3, 100 pM of NP-4, 100 pM of NP-5, 10 pM of NP-6, 1 nM of NP-8, or 10 pM of NP-9. Thereafter, the media containing various concentrations of LDH and 10% FBS were substituted with an assay medium containing 1% FBS before incubation for 24 his with three-day accumulated, 25 µM Aβ(25-35) (Peptron, Korea). The assay medium was free of phenol-red so that the medium could be monitored for color change while the reaction between released LDH and the reagents was ongoing. Then, the LDH reactant, composed of the enzyme and the dye, was incubated at RT for 10 min with the assay medium and the reaction was terminated with the stop solution of the assay kit, followed by measuring the absorbance at 492 nm and 690 nm on an ELISA reader. This LDH assay was performed in triplicate on three separate media.

Figure 4:
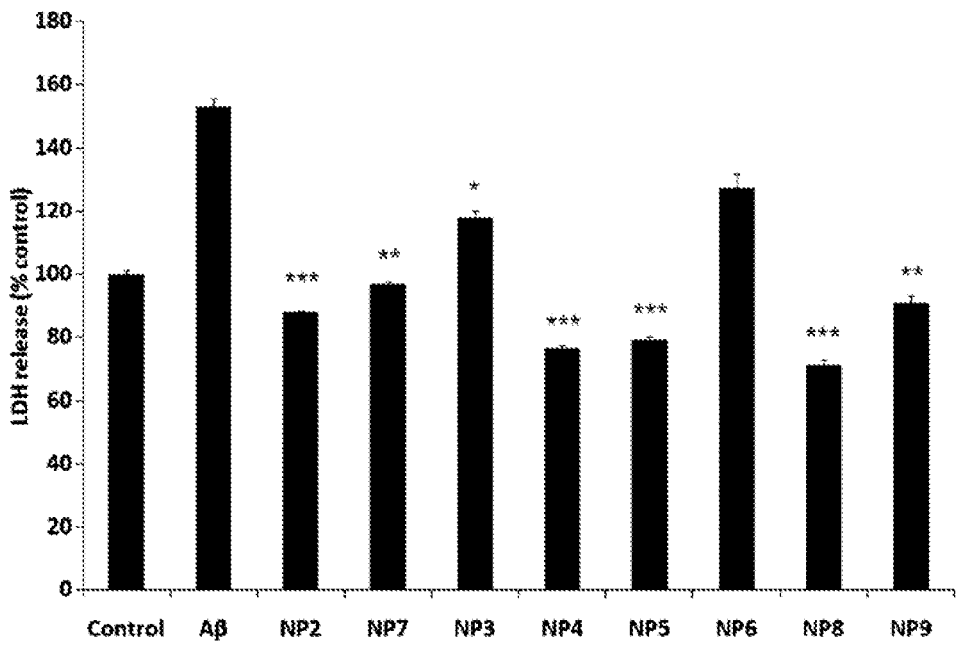
FIG. 4 is a graph showing the cytopotective effects of the synthetic peptides NP2 to NP9 upon LDH assay for anti-Parkinson's disease activity.

The assay results are shown in FIG. 4 in which values of experimental groups are represented as percentages relative to the control set as 100%. As is apparent from the data of FIG. 3, all the experimental groups exhibited significantly lower LDH releases than did the Aβ-treated group, indicating that the peptides of the present invention are cytoprotective against and therapeutic for Alzheimer's disease.

What is claimed is:

1. An isolated peptide for augmenting expression of BDNF (Brain-derived neurotrophic factor), having the following amino acid sequence: N'-$(Z_1)_\alpha$-$Z_2$-$(Z_3)_\beta$-C' wherein, N' is an N-terminus of the peptide and C' is a C-terminus of the peptide;
   $Z_1$ is G, M or R;
   $Z_2$ is D, T or V;
   $Z_3$ is F, G or Q;
   $\alpha$ is 0 or 1; and $\beta$ is 0 or 1, with a proviso that the peptide includes at least one of $Z_1$=M, $Z_2$=V and $Z_3$=G, both $\alpha$ and $\beta$ are not 0, and the peptide is not M-V-Q, V-G, M-V and M-T.

2. The peptide according to claim 1, having an amino acid sequence selected from a group consisting of G-V-G, R-V-G, M-D-G, M-T-G, M-V-F, and M-V-G.

3. The peptide according to claim 1, wherein the terminus N' or C' is acetylated or amidated.

4. The peptide according to claim 1, wherein the peptide augments the expression of BDNF in dopamine-reactive, human cells.

5. A pharmaceutical composition for treating neuropathy, comprising the peptide of claim 1 in a therapeutically effective amount, the neuropathy being selected from a group consisting of Alzheimer's disease, Parkinson's disease, chronic stress-related mood disorder, stroke, Huntington's disease, schizophrenia, obsessive compulsive disorder, Rett syndrome, dementia, anorexia nervosa, bulimia nervosa, obesity, cerebral ischemia, neurodegenerative disease, and diabetic neuropathy.

* * * * *